United States Patent
Zeller

(10) Patent No.: US 9,125,752 B2
(45) Date of Patent: Sep. 8, 2015

(54) URINE COLLECTION APPARATUS

(76) Inventor: Lewis N. Zeller, Vermillion, OH (US)

( * ) Notice: Subject to any disclaimer, the term of this patent is extended or adjusted under 35 U.S.C. 154(b) by 0 days.

(21) Appl. No.: 14/002,612

(22) PCT Filed: Feb. 21, 2012

(86) PCT No.: PCT/US2012/025955
§ 371 (c)(1),
(2), (4) Date: Aug. 30, 2013

(87) PCT Pub. No.: WO2012/118643
PCT Pub. Date: Sep. 7, 2012

(65) Prior Publication Data
US 2013/0338615 A1    Dec. 19, 2013

Related U.S. Application Data

(60) Provisional application No. 61/447,902, filed on Mar. 1, 2011.

(51) Int. Cl.
*A61F 5/44* (2006.01)
*A61F 5/441* (2006.01)

(52) U.S. Cl.
CPC ............... *A61F 5/4405* (2013.01); *A61F 5/441* (2013.01); *A61F 5/4407* (2013.01)

(58) Field of Classification Search
CPC ...... A61F 5/4405; A61F 5/4407; A61F 5/441
USPC .................................. 604/324, 327
See application file for complete search history.

(56) References Cited

U.S. PATENT DOCUMENTS

| | | | |
|---|---|---|---|
| 2,883,985 A | 4/1959 | Evans | |
| 3,661,143 A * | 5/1972 | Henkin | 600/575 |
| 4,417,892 A * | 11/1983 | Meisch | 604/323 |
| 7,438,473 B2 * | 10/2008 | Borchardt | 383/103 |
| 2006/0079854 A1 | 4/2006 | Kay et al. | |
| 2006/0271019 A1 | 11/2006 | Stoller et al. | |
| 2011/0046514 A1 | 2/2011 | Greenwald et al. | |

* cited by examiner

*Primary Examiner* — Leslie Deak
*Assistant Examiner* — Kai Weng
(74) *Attorney, Agent, or Firm* — Rankin, Hill & Clark LLP

(57) ABSTRACT

A urine collection apparatus is disclosed to include an expandable bag connected to a urinary catheter, the bag being adapted to receive urine expelled from the person using the apparatus. The apparatus also has a check valve associated with the bag, which opens to admit gas to the interior of the bag to equilibrate the pressure within the bag with the pressure of the surrounding atmosphere whenever a partial vacuum occurs in the bag.

6 Claims, 3 Drawing Sheets

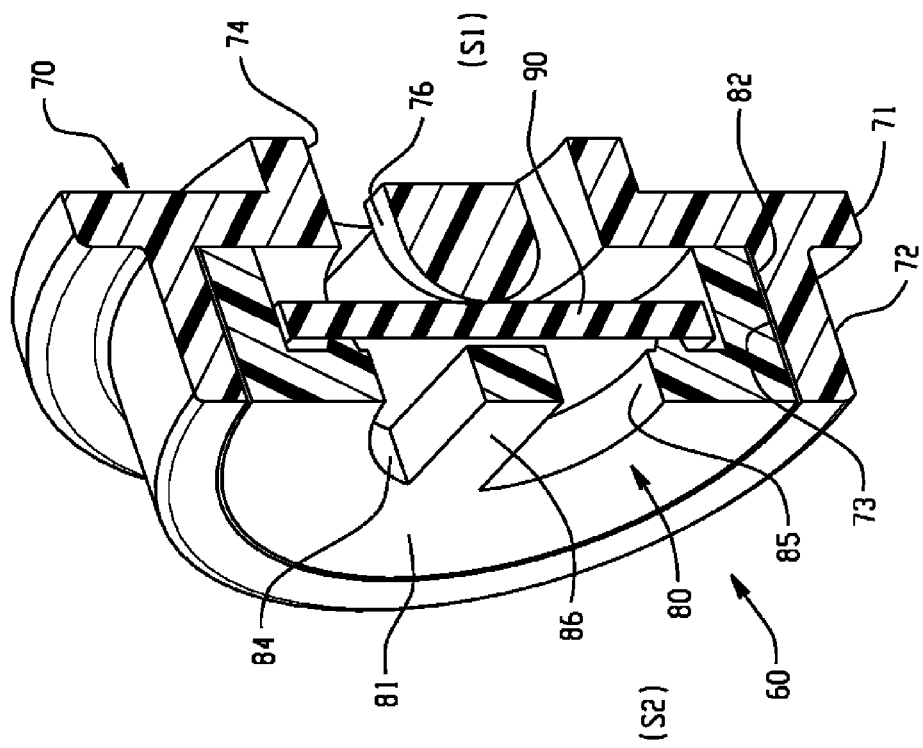
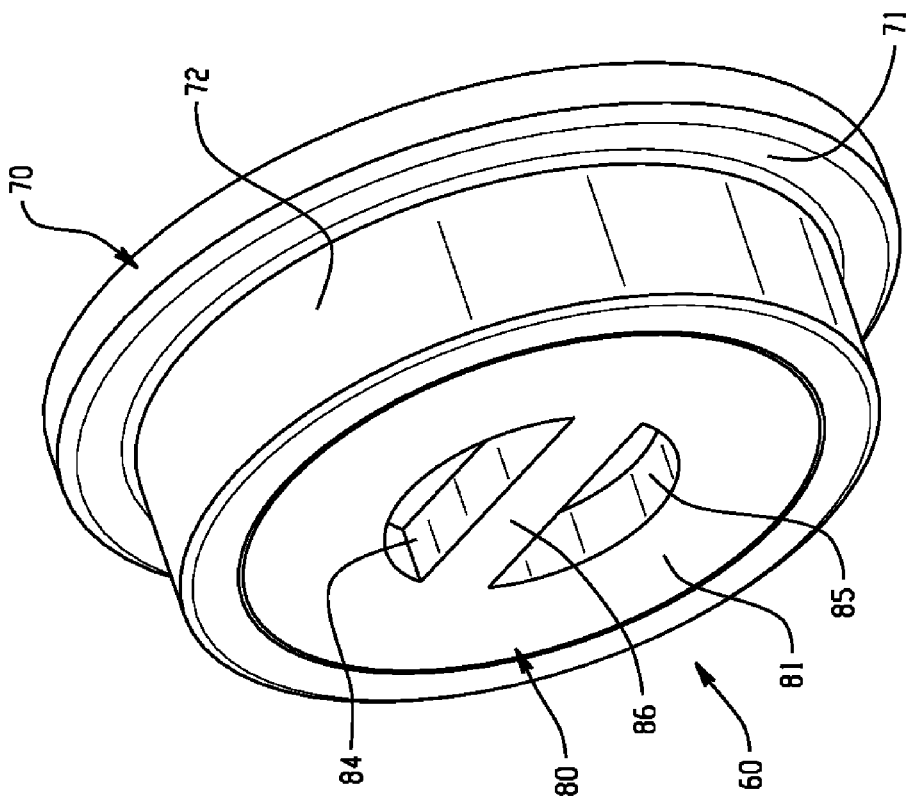
Fig. 4
Fig. 3

URINE COLLECTION APPARATUS

BACKGROUND OF THE INVENTION

1. Field of the Invention

This invention relates to receptacles or bags for receiving urine expelled from a person using a medical urine collection device. Such devices may include urinary catheters, Foley catheters, supra pubic catheters, external incontinence devices and others. Urine expelled by the user through these types of devices is accumulated in a urine collection bag such as a "leg bag".

2. Description of Related Art

The configuration of many conventional urine collection bags gives rise to a problem referred to as the "Siphon Effect". The Siphon Effect refers to a phenomenon whereby negative pressure accumulates in the urinary drainage tubing and urine collection bag as urine descends through the drainage tubing. As expelled urine drops into the urine collection bag, negative pressure accumulates behind the column of urine, causing a partial vacuum in the tubing. In the case of external catheters, the vacuum tends to draw external genitor-urinary tissue toward the proximal end of the drainage tubing, at times causing pain due to skin irritation, swelling and suction force injuries of the genitor urinary tissue. Excessive wear or premature detachment of external catheters may also result from the suction caused by the Siphon Effect.

In the case of indwelling catheter users, the vacuum forces generated by the Siphon Effect impinge on the inner surface of the bladder by drawing bladder vesicle neck tissue into the drainage port of the indwelling catheter, resulting in vesicle neck irritation. Vesicle neck irritation may enhance bacterial colonization of the bladder, increasing the risk of urinary-catheter-associated urinary tract infections.

Another problem caused by negative pressure in the urine collection bag is referred to as the "Urine Backup Phenomenon". As described above, as urine descends through the tubing to the collection bag, negative pressure is generated within the tube and within the collection bag. Many urine collection bags are constructed with an anti-reflux valve through which the urine must pass. As the urine drops through the anti-reflux valve and into the collection bag, the anti-reflux valve prevents equalization of the pressure differential between the drainage tubing and the bag. Since the collection bag may hold fifty times the volume of the tubing, the pressure differential increases considerably. This relatively large differential can cause the anti-reflux valve to remain closed, requiring greater force for the urine to exit the tubing when passing through the anti-reflux valve. Due to this increase in negative pressure within the collection bag, urine "backs up" in drainage tubing above the anti-reflux valve. This backup of urine may cause urine reflux into the urine collection device, and may push urine into contact with the user, creating the above stated problems associated with urine reflux.

Kay et al. (U.S. App. Pub. No. US 2006/0079854 A1) propose to alleviate the Siphon Effect and the Urine Backup Phenomenon primarily by eliminating the intermediate tubing between the urinary collection device and the collection bag. Unfortunately, this solution also inhibits the location of the collection bag. Kay et al also suggest that a "vent" can be used to allow ingress of air into the collection bag to equilibrate the pressure of the surrounding atmosphere and the pressure within the bag. "Vents" of this nature are known in the art.

Applicant has personally experienced pain, which he attributes to the so-called Siphon Effect, while using Foley catheters and suprapubic catheters. Applicant noticed that the pain was greater when he used an "unvented" leg bag than when he used a "vented" bedside bag. On at least one occasion, applicant heard an audible suction noise upon releasing the partial vacuum within the bag. This was accompanied by an immediate alleviation of pressure and pain.

As noted above, vented urine collection bags are known in the art. The vents disclosed generally comprise an air-permeable pad with randomly oriented fibers. When dry, the vent allows air to migrate into the collection bag. This equilibrates pressure inside and outside the bag, preventing the Siphon Effect from causing pain.

Unfortunately, vents are rarely used in leg bags. This is probably attributable to the fact that the vents cease to function as intended once they become wet, such as often occurs when the collection bag is strapped to a patient's leg. Vents of the type described can also cease to function as intended after they are washed using a vinegar solution.

Another factor that may contribute to the vacuum problem in such appliances is the effect of the weight of accumulated urine on the way in which the collection bag expands from an empty collapsed condition to an enlarged condition as urine is received from the collection device. As urine collects, the interior volume of the bag develops a urine component in the lower portion of the bag, but the upper portion of the bag remains in a collapsed condition. The urine component assumes a bulged out condition due to hydrostatic forces and the lower portion of the bag expands accordingly.

On the other hand, the volume of the upper portion of the bag does not increase significantly as urine collects in the lower portion of the bag. The result is that the upper portion of the bag is somewhat "curved" due to the weight of the urine and the walls of the upper portion of the bag are urged outwardly to try to accommodate the increased width of the expanded lower portion of the bag. The resulting forces acting to increase the width of the upper portion of the bag tend to create a partial vacuum, which may cause discomfort.

The collection bag of the present invention reduces the difficulties described above and affords other features and advantages heretofore not obtainable.

SUMMARY OF THE INVENTION

In view of the foregoing, the present invention is directed toward a collection bag with a check valve that is impervious to the urine accumulated within the bag. The valve allows air to enter the collection bag as necessary to equilibrate the pressure inside and outside of the bag and thereby negate the pain and other complications attributable to the Siphon Effect and other forces that may cause the creation of a partial negative pressure within the collection bag. Unlike the vents used in some collection bags, the check valve does not cease to function as intended when exposed to urine, other bodily fluids and/or cleaning solutions.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

BRIEF DESCRIPTION OF THE DRAWINGS

FIG. 3 is an enlarged perspective view looking toward the front face of the one-way check valve used in the collection bag of FIG. 1.

FIG. 4 is an enlarged perspective view looking toward the front face of the one-way check valve of FIG. 3 with parts broken away and shown in section.

DETAILED DESCRIPTION OF THE INVENTION

Figure 1:
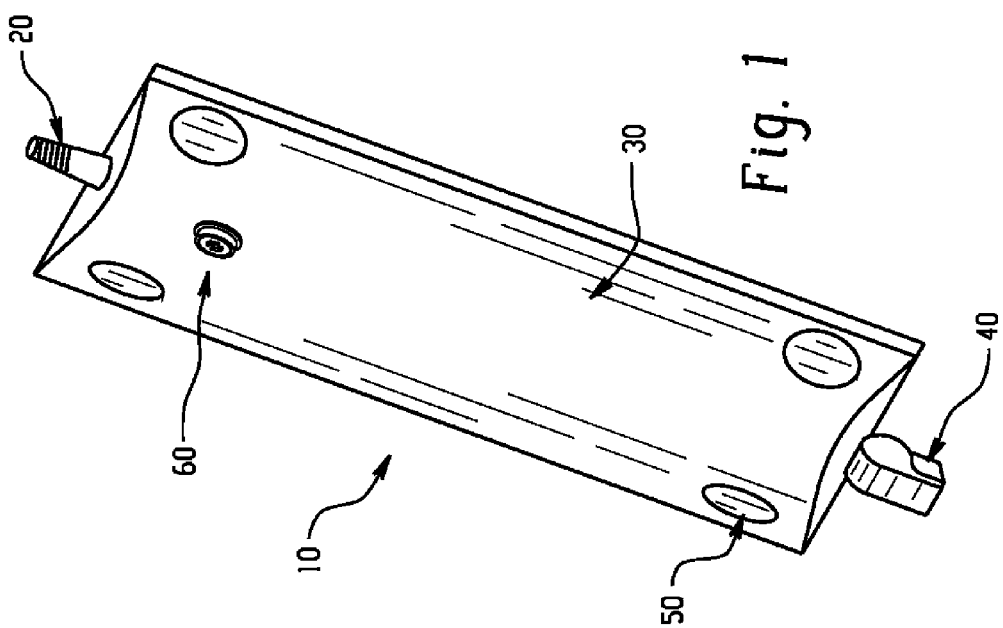
FIG. 1 is a perspective view showing a urine collection bag having a one-way check valve in accordance with the invention.

FIG. 1 shows an expandable plastic urine collection apparatus 10 adapted to be strapped to the leg of a patient fitted with a catheter. Urine travels through the catheter (not shown) to a liquid inlet tube 20 that delivers urine into a flexible plastic bag 30 which is part of the apparatus 10. The bag 30, being made of plastic film, can expand from a collapsed condition to a non-collapsed condition as necessary to accommodate urine that enters through the inlet tube 20. The apparatus 10 is also optionally fitted with a liquid outlet tube 40 that can be used to empty urine collected in the bag 30. Also, the apparatus can be fitted with conventional button leg strap fasteners 50, such as are known in the art. The button leg strap fasteners allow the apparatus to be temporarily secured to a user's leg, typically with elastic straps. In other embodiments, the bag 30 can be secured to (e.g., suspended from) a bedside structure rather than to the patient's leg. In accordance with the invention, a one-way check valve 60 is provided in the bag 30.

Figure 2:
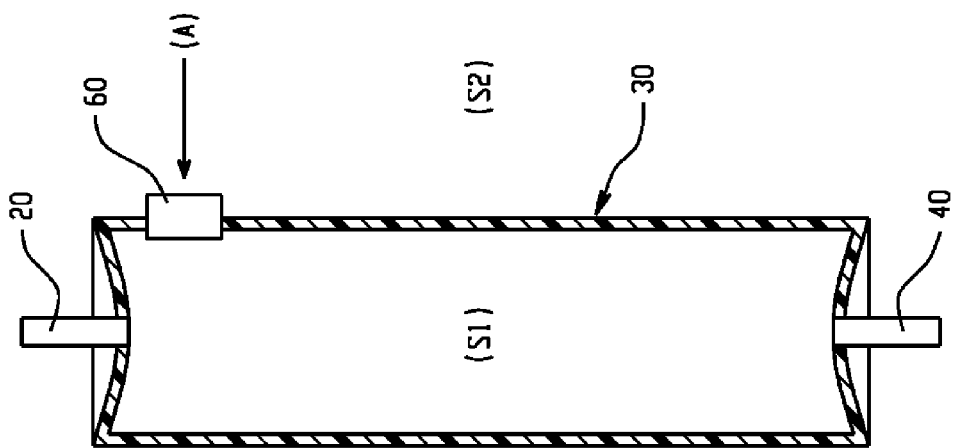
FIG. 2 is a diagrammatic sectional view of the collection bag of FIG. 1 taken perpendicular to the longitudinal axis through the one-way check valve.

With reference to FIG. 2, the check valve 60 allows air (A) to enter an interior side (S1) of the bag 30 from an exterior side (S2) to substantially equilibrate the pressure within the bag with atmospheric pressure. The location of the check valve 60 on the bag 30 is not per se critical. But it is generally considered to function best when positioned at the midline of the bag or higher, but preferably not in the direct urine stream entering the bag through the inlet 20. Also, the valve may be placed in the liquid inlet tube 20, or in a gas-filled passageway that surrounds the liquid inlet tube 20 (not shown).

Figure 5:
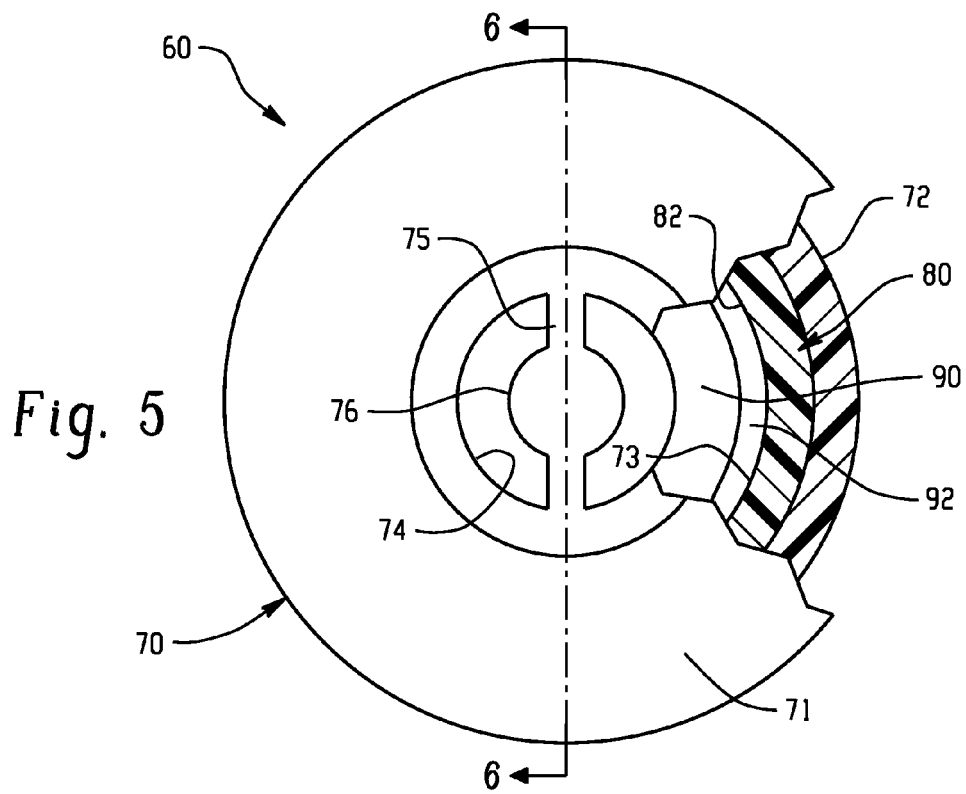
FIG. 5 is a rear elevation of the one-way check valve of FIGS. 3 and 4 with parts broken away and shown in section.

FIGS. 3 through 7 illustrate the construction and operation of an exemplary one-way check valve 60. The valve shown is only typical of the various types of suitable check valves that may be used in the practice of the invention. FIGS. 3 and 4 show the valve 60 as viewed from the front, the front or forward end of the valve being located on the outside of the collection bag 30 facing the surrounding atmosphere. The rearward end of the valve as viewed in FIG. 5 is positioned to face into the interior of the collection bag 30, where it may contact urine during use. The valve is preferably welded, e.g. by ultrasonic welding or by radio frequency welding, or otherwise permanently sealed to the bag 30.

The check valve 60 includes as its primary components, a housing 70, a valve seat 80 and a valve disc 90. The housing 70 and the valve seat 80 are typically formed of molded plastic material and the valve disc is preferably formed of flexible resilient elastomeric material.

The housing 70 has a flat circular base portion 71 and an annular wall 72 extending in a forward direction from the periphery of the base portion. The wall 72 and the front face of the base portion 71 define a recess 73 that receives the valve seat 80 and the valve disc 90.

The base portion 71 also defines an opening 74 that serves as an exit port for the valve 70. A beam 75 extends across the opening 74 as shown in FIG. 5, to provide a support for a valve disc positioning pin 76. The pin 76 engages the center of the disc 90 and serves to locate and retain the disc in its proper operating position as will be described below.

The valve seat 80 has a flat circular end portion 81 and an annular wall 82 extending in a rearward direction from the periphery of the end portion 81. The wall has an outer diameter approximately the same as the inner diameter of the annular wall 72 so that the housing 70 may receive the valve seat 80 and the valve disc 90 as best shown in FIGS. 6 and 7.

Figure 6:
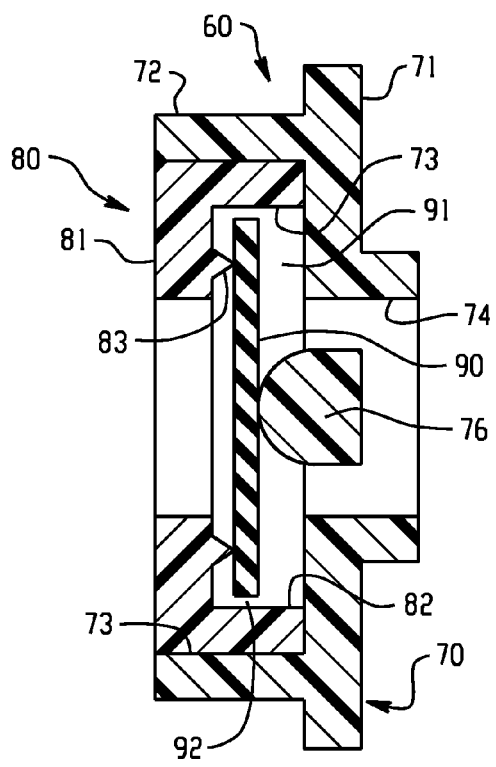
FIG. 6 is a sectional view of the one-way check valve of FIGS. 3, 4 and 5, taken on the line 6-6 of FIG. 5, and showing the valve in its closed condition.

The inner face of the end portion 81 has a circular ridge 83 that is engaged by the forward face of the valve disc 90 when the valve is in its closed position as shown in FIG. 6. The end portion 81 also defines a pair of openings 84 and 85 that are separated by a beam 86. The openings 84 and 85 serve as entry ports for air entering the valve 60.

The valve disc 90 is positioned in a chamber 91 defined by the housing 70 and the valve seat 80. The disc is urged against the circular ridge 83 of the valve seat by the positioning pin 76 which engages the center of the disc only. Accordingly, the disc is able to flex rearwardly about its center away from the circular ridge in the manner shown in FIG. 7. The disc 90 has an outer diameter somewhat less than the inner diameter of the annular wall 82 so as to define a gap 92 that permits gas to flow from one side of the valve disc to the other when the valve is in its open position.

Figure 7:
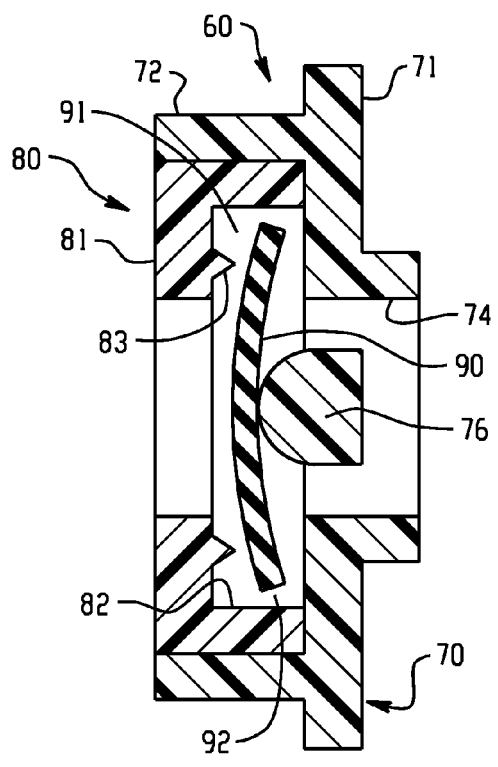
FIG. 7 is a sectional view of the one-way check valve of FIGS. 3, 4 and 5, similar to FIG. 6, and showing the valve in its open condition.

The operation of the valve 60 is best illustrated in FIGS. 6 and 7. FIG. 6 shows the valve in its closed position to seal the interior volume (S1) of the collection bag 30 from the surrounding atmosphere (S2). This position would result when the pressure of the gaseous component (S1) in the bag 30 is approximately equal to the pressure of the surrounding atmosphere (S2). In this position, the forward face of the valve disc 90 engages the circular ridge 83 of the valve seat 80.

FIG. 7 illustrates the check valve 60 in its open position to admit gas from the surrounding atmosphere (S2) into the gaseous component (S1) of the interior of the bag 30. The valve disc 90 will flex as shown in FIG. 7 into its open position when the pressure of the gaseous component (S2) in the bag 30 is less than the pressure of the surrounding atmosphere (S1) or in other words when there is a partial vacuum in the bag. Accordingly, when the valve disc 90 disengages from the circular ridge 83, a passage through the valve is opened. As a result, gas flows through the inlet ports 84 and 85, radially outward to the outer edge of the flexed valve disc 90, across the gap 92, radially inward to the outlet port 74 and then out through the outlet port 74 into the interior (S1) of the collection bag.

It will be appreciated that a two-way check valve could be used, if desired and that a variety of check valve configurations could be used within the spirit of the invention. Applicant has confirmed that vacuum release valves presently used to allow for degassing of bagged coffee are suitable for use in practicing the invention. It will be further appreciated that the invention can be used in other applications such as, for example, providing a waterproof vacuum release valve in an ostomy bag.

Thus the present invention overcomes the limitations of the prior art. The "vents" in prior art leg and overnight bags do not function properly when exposed to fluid such as urine or cleaning solutions. Other solutions to negate the Siphon Effect place inconvenient limitations regarding the position of the bag. A urine collection bag according to the invention can be washed and reused repeatedly without losing its intended function.

While the invention has been shown and described with respect to a specific embodiment thereof, this is intended for the purpose of illustration rather than limitation and other variations and modifications of the specific embodiment herein shown and described will be apparent to those skilled in the art, all within the spirit and scope of the invention. Accordingly, the patent is not to be limited in scope and effect to the specific embodiment shown and described, nor in any other way that is inconsistent with the extent to which the progress in the art has been advanced by the invention.

The invention claimed is:

1. A urine collection apparatus for collecting urine expelled from a person fitted with a urinary catheter, the urine collection apparatus comprising:
   a bag formed of plastic film defining an interior volume in fluid communication with the urinary catheter, said bag being capable of expanding from an empty collapsed condition to an enlarged non-collapsed condition upon receipt of urine from the urinary catheter, wherein in the enlarged non-collapsed condition the interior volume of the bag is occupied at least in part by urine; and
   a check valve located in an upper portion of said bag, said check valve comprising
       a housing welded to the plastic film that forms the bag,
       a valve seat, and
       a flexible valve disc,
   wherein said check valve is configured to be in a closed position with the valve disc engaged with the valve seat to seal said interior volume from a surrounding atmosphere when pressure within said bag is approximately equal to pressure of the surrounding atmosphere,
   wherein said check valve is configured to open to an open position with the valve disc flexed and disengaged from the valve seat to admit gas from the surrounding atmosphere into the bag when the pressure within said bag is less than the pressure of the surrounding atmosphere,
   wherein said check valve functions to substantially equilibrate the pressure within the bag with the pressure of said surrounding atmosphere as urine is received from the urinary catheter,
   wherein the check valve has an interior side that faces the interior volume of the bag and an exterior side that faces the surrounding atmosphere, and
   wherein the check valve continues to function notwithstanding that the interior side of the check valve has been contacted by urine.

2. The urine collection apparatus according to claim 1, wherein said check valve is a one-way check valve.

3. The urine collection apparatus according to claim 1, further comprising:
   an entry tube located in said upper portion and being operatively connected to said urinary catheter, said entry tube defining a passageway to the interior volume of the bag.

4. The urine collection apparatus according to claim 1 further including an outlet tube located in a lower portion of said bag.

5. The urine collection apparatus according to claim 1, wherein the apparatus is configured for attachment to a leg of a person fitted with the urinary catheter.

6. The urine collection apparatus according to claim 1, wherein said check valve is a two-way check valve.

* * * * *